United States Patent
Lee et al.

(10) Patent No.: US 7,452,569 B2
(45) Date of Patent: Nov. 18, 2008

(54) ORGANIC ALUMINUM PRECURSOR AND METHOD OF MANUFACTURING A METAL WIRING USING THE SAME

(75) Inventors: Jung-Ho Lee, Suwon-si (KR); Jung-Sik Choi, Seongnam-si (KR); Jun-Hyun Cho, Suwon-si (KR); Youn-Joung Cho, Suwon-si (KR); Tae-Sung Kim, Suwon-si (KR); Mi-Ae Kim, Seoul (KR); Kyoo-Chul Cho, Yongin-si (KR)

(73) Assignee: Samsung Electronics Co., Ltd., Suwon-si, Gyeoggi-do (KR)

( * ) Notice: Subject to any disclaimer, the term of this patent is extended or adjusted under 35 U.S.C. 154(b) by 37 days.

(21) Appl. No.: 11/524,295

(22) Filed: Sep. 21, 2006

(65) Prior Publication Data

US 2007/0071893 A1   Mar. 29, 2007

(30) Foreign Application Priority Data

Sep. 26, 2005   (KR) .................. 10-2005-0089276

(51) Int. Cl.
- C23C 16/00 (2006.01)
- C23C 16/06 (2006.01)
- B05D 7/22 (2006.01)
- H05H 1/24 (2006.01)

(52) U.S. Cl. .............. 427/248.1; 427/255.29; 427/255.31; 427/255.28; 427/230; 427/569; 427/250; 427/249.5; 427/255.32; 427/255.6

(58) Field of Classification Search ............ 427/255.29, 427/255.31, 255.28, 230, 569, 250, 248.1, 427/249.5, 255.32, 255.6; 556/172, 176
See application file for complete search history.

(56) References Cited

U.S. PATENT DOCUMENTS

| | | | | |
|---|---|---|---|---|
| 6,130,160 A | * | 10/2000 | Vaartstra | ................... 438/681 |
| 2004/0026786 A1 | | 2/2004 | Leu et al. | |
| 2006/0257567 A1 | * | 11/2006 | Peters et al. | ............. 427/248.1 |

FOREIGN PATENT DOCUMENTS

| | | |
|---|---|---|
| JP | 2000-086673 | 3/2000 |
| KR | 100246155 B1 | 12/1999 |
| KR | 100292687 B1 | 3/2001 |

OTHER PUBLICATIONS

Glass et al, Chemical Vapor Deposition Precursor Chemistry. Formation of Pure Aluminum, Alumina, and Aluminum Boride Thin Films from Boron-Containing Precursor Compounds by Chemical Vapor Deposition, Chemistry of Materials, 4, 530-538.*

* cited by examiner

*Primary Examiner*—Timothy Meeks
*Assistant Examiner*—Kelly M Stouffer
(74) *Attorney, Agent, or Firm*—Volentine & Whitt, PLLC (57) ABSTRACT

In a method of manufacturing a metal wiring, an organic aluminum precursor that includes aluminum as a central metal is applied to a substrate. The organic aluminum precursor applied to the substrate is thermally decomposed to form aluminum. The aluminum is deposited on the substrate to form an aluminum wiring having a low resistance. The organic aluminum precursor includes a chemical structure in accordance with one of the chemical formulae:

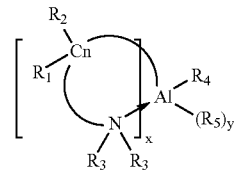

wherein $R_1$, $R_2$, $R_3$, $R_4$ and $R_5$ are independently H or a $C_1$-$C_5$ alkyl functional group, n is an integer of 1 to 5, x is 1 or 2, and y is 0 or 1, or

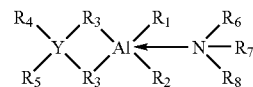

wherein $R_1$, $R_2$, $R_3$, $R_4$ $R_5$, $R_6$, $R_7$ and $R_8$ are independently H or a $C_1$-$C_5$ alkyl functional group, and Y is boron.

7 Claims, 4 Drawing Sheets

ORGANIC ALUMINUM PRECURSOR AND METHOD OF MANUFACTURING A METAL WIRING USING THE SAME

BACKGROUND OF THE INVENTION

1. Field of the Invention

Example embodiments of the present invention relate to an organic aluminum precursor and a method of manufacturing a metal wiring using the same. More particularly, example embodiments of the present invention relate to an organic aluminum precursor that may be used in a chemical vapor deposition (CVD) process or a cyclic CVD process, and a method of manufacturing a metal wiring using the organic aluminum precursor.

A claim of priority under 35 USC § 119 is made to Korean Patent Application No. 2005-89276, filed on Sep. 26, 2005, the contents of which are herein incorporated by reference in its entirety for all purposes.

2. Description of the Related Art

In order to fabricate a high speed and large capacity semiconductor device, it is necessary that the metal conductive structures that transmit electric signals in the semiconductor device have favorable electrical characteristics.

The metal conductive structures in the semiconductor device are usually formed of aluminum (Al), tungsten (W) or copper (Cu). Aluminum has a lower specific resistance relative to that of tungsten. In addition, an aluminum layer pattern may be formed by a dry etching process unlike a copper layer pattern. Thus, aluminum is widely used to form a conductive structure such as a contact, a plug and a wire.

An aluminum wire is usually formed by a plasma vapor deposition (PVD) process such as a sputtering process. However, as an aspect ratio of a via or a contact hole increases, the formation of the aluminum wire by the PVD process has reached its limit.

As a result, a chemical vapor deposition (CVD) process has been applied to form an aluminum wire. A precursor used in a CVD process includes, for example, trimethyl aluminum (TMA), dimethyl aluminum hydride (DMAH) or triisobutyl aluminum (TIBA).

The above-mentioned precursors have a high vapor pressure, which is consider advantageous because the precursor may be easily deposited by a CVD process. However, the CVD process requires a high temperature of about 250° C. to about 400° C. In addition, the aluminum wire may include impurities such as carbon, thereby increasing an electric resistance.

In order to avoid these problems, a deposition process using a dimethylethyl amine alane (DMEAA) precursor has been studied. The DMEAA precursor has a high vapor pressure and is deposited at a temperature of about 100° C. to about 200° C. However, the DMEAA precursor is thermally unstable at a room temperature. Hence, a deposition process using a more stable methyl pirolidine alane (MPA) precursor has been suggested. A method of forming an aluminum wire using the MPA precursor is disclosed in Korean Laid-Open Patent Publication No. 2000-0022650. Although the MPA precursor is more thermally stable than the DMEAA precursor, the MPA precursor is also thermally and chemically unstable at a temperature above about 30° C. Hence, when the MPA precursor is introduced into a chamber by a CVD process, the MPA precursor may remain as particles in the chamber and fall on the aluminum wire during formation of the aluminum wire or after formation of the aluminum wire.

SUMMARY OF THE INVENTION

An organic aluminum precursor which may be used to form an aluminum wiring in a semiconductor device in accordance with one aspect of the present invention includes a chemical structure in accordance with chemical formula 1 shown below:

Chemical Formula 1 wherein $R_1$, $R_2$, $R_3$, $R_4$ and $R_5$ are independently H or $C_1$-$C_5$ alkyl functional group, n is an integer of 1 to 5, x is 1 or 2, and y is 0 or 1.

According to one example embodiment, x is 1 and y is 1, and the organic aluminum precursor includes a chemical structure in accordance with chemical formula 2 shown below:

Chemical Formula 2

According to another example embodiment, x is 2 and y is 0, and the organic aluminum precursor includes a chemical structure in accordance with chemical formula 3 shown below:

Chemical Formula 3

Examples of the above organic aluminum precursor may include a dimethylamino-2-methylpropyl methyl aluminum hydride precursor.

An organic aluminum precursor used for forming an aluminum wiring of a semiconductor device in accordance with another aspect of the present invention includes a chemical structure in accordance with chemical formula 4 shown below:

Chemical Formula 4 wherein $R_1$, $R_2$, $R_3$, $R_4$ $R_5$, $R_6$, $R_7$ and $R_8$ are independently H or $C_1$-$C_5$ alkyl functional group, and Y is boron (B). Particularly, the organic aluminum precursor represented by the chemical formula 4 may include an aluminum boro-hydride trialkylamine precursor.

In a method of manufacturing a metal wiring in accordance with still another aspect of the present invention, an organic aluminum precursor that includes aluminum as a central metal and includes a chemical structure in accordance with chemical formula 1 or 4 is applied to a substrate. The organic aluminum precursor applied to the substrate is thermally decomposed to form aluminum. The aluminum is thus deposited on the substrate to form an aluminum wiring.

According to one example embodiment, the organic aluminum precursor may be applied to the substrate with a carrier gas. Examples of the carrier gas may include argon, helium, neon or nitrogen.

BRIEF DESCRIPTION OF THE DRAWINGS

The above and other features and advantages of the invention will become readily apparent by reference to the detailed description that follows when considered in conjunction with the accompanying drawings, wherein.

DESCRIPTION OF THE EMBODIMENTS

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Organic Aluminum Precursor 1

An organic aluminum precursor of one example embodiment may be used to form an aluminum layer or an aluminum wiring. The organic aluminum precursor exhibits favorable evaporation characteristics at relatively low temperatures. Further, productivity may be enhanced by using the organic aluminum precursor in a CVD process or a cyclic CVD process to form an aluminum layer.

The organic aluminum precursor includes aluminum as a central metal and at least two kinds of ligands having strong bonding strength with respect to the aluminum. The organic aluminum precursor of this example includes a chemical structure in accordance with chemical formula. 1:

Chemical Formula 1

In the chemical formula 1, $R_1$, $R_2$, $R_3$, $R_4$ and $R_5$ are independently H or a $C_1$-$C_5$ alkyl functional group, n is an integer of 1 to 5, x is 1 or 2, and y is 0 or 1.

In the preceding paragraph, the word "independently" means that $R_1$ through $R_5$ can either be the same as each other or different from each other, i.e., the choice of H or a $C_1$-$C_5$ alkyl functional group for each of $R_1$ through $R_5$ is not dependent upon the choice of H or a $C_1$-$C_5$ alkyl functional group for each of the remaining of $R_1$ through $R_5$.

In an example, x is 1 and y is 1 in the chemical formula 1, and the organic aluminum precursor includes a chemical structure in accordance with chemical formula 2:

Chemical Formula 2

In the chemical formula 2, $R_1$, $R_2$, $R_3$, $R_4$ and $R_5$ are independently H or a $C_1$-$C_5$ alkyl functional group, and n is an integer of 1 to 5.

In another example, x is 2 and y is 0 in the chemical formula 1, and the organic aluminum precursor includes a chemical structure in accordance with chemical formula 3:

Chemical Formula 3

In the chemical formula 3, $R_1$, $R_2$, $R_3$ and $R_4$ are independently H or a $C_1$-$C_5$ alkyl functional group, and n is an integer of 1 to 5.

Particularly, an example of the organic aluminum precursor of the chemical formulae 1 and 2 may include dimethylamino-2methylpropyl methyl aluminum hydride.

The organic aluminum precursor represented by the chemical formulae 1 through 3 may be used in a CVD process or a cyclic CVD process to form an aluminum layer or an aluminum wiring.

The organic aluminum precursor of above examples may exhibit greater thermal and chemical stability than that of an MPA precursor. Further, while the organic aluminum precursor flows through a gas line of a CVD apparatus for forming an aluminum layer, the organic aluminum precursor may exhibit greater stability against a mechanical or physical impact than that of an MPA precursor. That is, while the organic aluminum precursor is introduced into a chamber of the CVD apparatus, the organic aluminum precursor in the gas line may not be decomposed.

Further, the organic aluminum precursor may be evaporated in a canister at a temperature of about 20° C. to about 60° C., preferably about 20° C. to about 50° C. Particularly, when the organic aluminum precursor in the canister is evaporated at a temperature of about 30° C., the organic aluminum precursor may have a vapor pressure of about 0.7 torr to about 1.0 torr, preferably about 0.8 torr to about 0.95 torr. When the organic aluminum precursor in the canister is evaporated at a temperature of about 60° C., the organic aluminum precursor may have a vapor pressure of about 1.1 torr to about 1.3 torr, preferably about 1.15 torr to about 1.25 torr.

Therefore, when the aluminum wiring is formed by a CVD process using the organic aluminum precursor, the organic aluminum precursor may be maintained as a liquid phase and may not undergo spontaneous combustion at a room temperature. Further, the organic aluminum precursor may exhibit thermal and chemical stability at a temperature of about 30° C., so that the organic aluminum precursor may not be decomposed at a temperature of about 30° C. As a result, defects may not be generated in the aluminum wiring, and thus a cleaning process for removing the defects with respect to the CVD apparatus may be unnecessary, thereby improving productivity of a semiconductor device including the aluminum wiring.

Organic Aluminum Precursor 2

An organic aluminum precursor of this example embodiment is used for forming an aluminum layer or an aluminum wiring. The organic aluminum precursor exhibits favorable evaporation characteristics at a low temperature. Further, productivity may be enhanced by using the organic aluminum precursor in a CVD process or a cyclic CVD process to form an aluminum layer.

The organic aluminum precursor of this example includes a chemical structure in accordance with chemical formula 4:

Chemical Formula 4

In the chemical formula 4, $R_1$, $R_2$, $R_3$, $R_4$ $R_5$, $R_6$, $R_7$ and $R_8$ are independently H or a $C_1$-$C_5$ alkyl functional group, and Y is boron (B).

In the preceding paragraph, the word "independently" means that $R_1$, through $R_8$ can either be the same as each other or different from each other, i.e., the choice of H or a $C_1$-$C_5$ alkyl functional group for each of $R_1$, through $R_8$ is not dependent upon the choice of H or a $C_1$-$C_5$ alkyl functional group for each of the remaining of $R_1$ through $R_8$.

In the chemical formula 4, $R_6$ and $R_7$ are connected to each other to form a ring. Further, boron (Y) is bonded to $R_3$ that is capable of being bridge-bonded to Al.

Particularly, $R_3$ of the organic aluminum precursor represented by the chemical formula 4 may be H or a methyl functional group. Further, the organic aluminum precursor may include an aluminum boro-hydride trialkylamine precursor. The organic aluminum precursor represented by the chemical formula 4 may be used in a CVD process for forming an aluminum layer or an aluminum wiring.

The organic aluminum precursor of this example may exhibit greater thermal and chemical stability than that of an MPA precursor. Further, while the organic aluminum precursor flows through a gas line of a CVD apparatus for forming an aluminum layer, the organic aluminum precursor may exhibit greater stability than that of an MPA precursor against mechanical or physical impact. That is, while the organic aluminum precursor is introduced into a chamber of the CVD apparatus, the organic aluminum precursor in the gas line may not be decomposed.

Further, the organic aluminum precursor may be evaporated in a canister at a temperature of about 20° C. to about 60° C., preferably 30° C. to about 40° C. Particularly, when the organic aluminum precursor in the canister is evaporated at a temperature of about 30° C., the organic aluminum precursor may have a vapor pressure of about 0.4 torr to about 0.6 torr, preferably about 0.45 torr to about 0.55 torr. When the organic aluminum precursor in the canister is evaporated at a temperature of about 50° C., the organic aluminum precursor may have a vapor pressure of about 1.2 torr to about 1.4 torr, preferably about 1.25 torr to about 1.35 torr.

Furthermore, the organic aluminum precursor of this example may be thermally decomposed at a temperature of about 80° C. to about 200° C. provided from a susceptor so that the ligands may be readily released from the aluminum as the central metal. That is, since a temperature of the susceptor for thermally decomposing the organic aluminum precursor represented by the chemical formula 4 may be no more than about 200° C., thermal stresses applied to a lower structure of the semiconductor substrate on which the aluminum wiring is to be formed may be lowered during formation of the aluminum wiring using the organic aluminum precursor.

Therefore, when the aluminum wiring is formed by a CVD process using the organic aluminum precursor, the organic aluminum precursor may exhibit thermal and chemical stability at a room temperature or higher. Furthermore, the organic aluminum precursor may not be decomposed due to mechanical and physical impact. As a result, defects may not be generated in the aluminum wiring so that a cleaning process for removing the defects with respect to the CVD apparatus may be unnecessary, thereby improving productivity of a semiconductor device including the aluminum wiring.

Method of Manufacturing an Aluminum Layer

Figure 1:
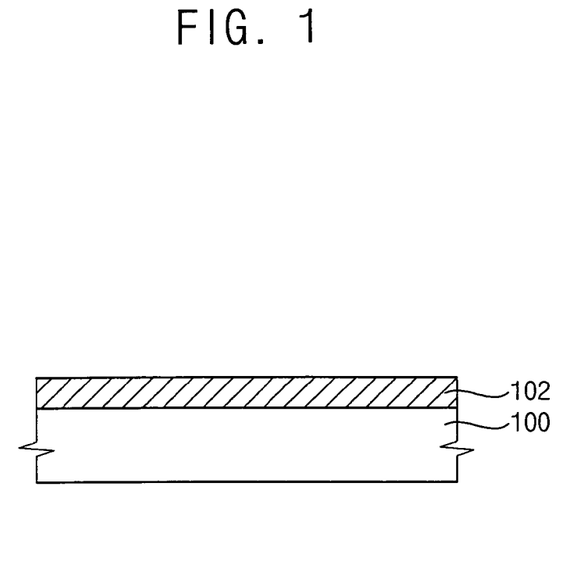
FIG. 1 is a cross-sectional view for describing a method of manufacturing an aluminum layer in accordance with an example embodiment of the present invention.

FIG. 1 is a cross-sectional view for describing a method of manufacturing an aluminum layer in accordance with an example embodiment of the present invention.

Referring to FIG. 1, a semiconductor substrate 100 is introduced into a CVD chamber. That is, the semiconductor substrate 100 is placed on a suscepter (not shown) in the CVD chamber. The chamber is set up to have a pressure and a temperature that is appropriate for performing the CVD process.

An organic aluminum precursor represented by one of the chemical formulae 1 through 4 is introduced over the semiconductor substrate 100 in the CVD chamber. Any further illustrations with respect to organic aluminum precursor are omitted herein for brevity. In this example embodiment, an example of the organic aluminum precursor represented by the chemical formula 1 is a dimethylamino-2-methylpropyl methyl aluminum hydride precursor. Further, an example of the organic aluminum precursor represented by the chemical formula 4 is an aluminum boro-hydride trialkylamine precursor.

Here, the organic aluminum precursor may be introduced into the CVD chamber as gaseous phase by a liquid delivery system (LDS), a bubbling system, etc. Further, the gaseous organic aluminum precursor may be introduced into the chamber with a carrier gas. Examples of the carrier gas may include an argon gas, a helium gas, a nitrogen gas or a neon gas. These can be used individually or in a combination of two or more thereof.

The gaseous organic aluminum precursor applied to the semiconductor substrate 100 on the suscepter is thermally decomposed to release the ligands from the aluminum as the central metal, thereby generating pure aluminum atoms. Here, the suscepter for supporting the semiconductor substrate 100 may have a temperature of about 80° C. to about 250° C., preferably about 80° C. to about 180° C. In this example embodiment, the semiconductor substrate 100 or the CVD chamber may have a temperature of about 130° C. to about 160° C.

The aluminum atoms formed by thermal decomposition of the organic aluminum precursor are deposited on an upper face of the semiconductor substrate 100 to form an aluminum layer 102 on the semiconductor substrate 100. The aluminum layer 102 may have an electrical resistance which is lower than that of an aluminum layer formed using an MPA precursor.

In this example embodiment, the aluminum layer is formed by a CVD process, or alternatively, the aluminum layer may be formed by a cyclic CVD process.

Method of Manufacturing a Semiconductor Device

FIGS. 2 to 6 are cross-sectional views for describing a method of manufacturing an aluminum wiring of a semiconductor device in accordance with an example embodiment of the present invention.

Figure 2:
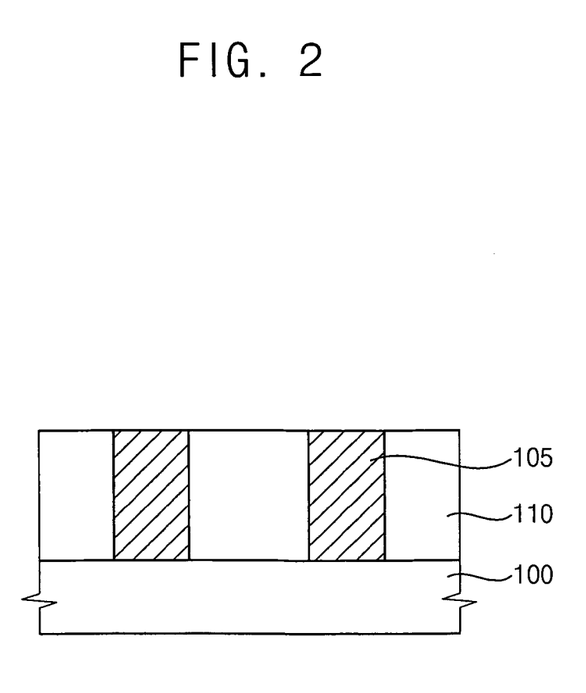
FIGS. 2 to 6 are cross-sectional views for describing a method of manufacturing an aluminum wiring of a semiconductor device in accordance with an example embodiment of the present invention.

FIG. 2 is a cross-sectional view illustrating a process of forming a first insulating interlayer pattern.

Referring to FIG. 2, a first insulating interlayer pattern 110 is formed on a substrate 100. The first insulating interlayer pattern 110 includes a contact 105 therein. The contact 105 is formed through the first insulating interlayer pattern 110 and is electrically connected to the substrate 100. The substrate 100 may include lower structures (not shown) thereon. The lower structures may include, for example, a bit line, a word line, a gate structure, a pad, a plug, and/or a metal wiring.

To form the first insulating interlayer pattern 110, a first insulating interlayer is formed on the substrate 100 to cover the lower structures. The first insulating interlayer may be formed, for example, using an oxide such as boro phosphor silicate glass (BPSG), phosphor silicate glass (PSG), undoped silicate glass (USG), spin on glass (SOG), plasma enhanced tetraethyl orthosilicate (PE-TEOS), or high density plasma-chemical vapor deposition (HDP-CVD) oxide. A contact hole is formed in the first insulating interlayer to expose the lower structures. The first insulating interlayer is patterned to form the first insulating interlayer pattern 110.

To form the contact 105, a conductive layer is formed on the first insulating interlayer pattern 110 to fill the contact hole. The conductive layer may be formed using a metal such as aluminum (Al). The conductive layer is partially removed by a chemical mechanical polishing (CMP) process or an etch back process or a combination of CMP and etch back to expose the first insulating interlayer pattern 110. Hence, the contact 105 is formed in the first insulating interlayer pattern 110.

Figure 3:
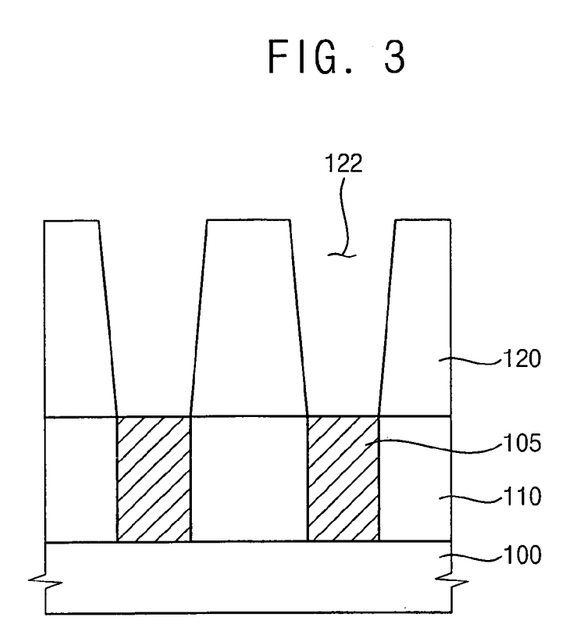

FIG. 3 is a cross-sectional view for describing a process of forming a second insulating interlayer pattern having an opening.

Referring to FIG. 3, a second insulating interlayer pattern 120 is formed on the contact 105 and the first insulating interlayer pattern 110. The second insulating interlayer pattern 120 includes an opening 122 exposing the contact 105.

To form the second insulating interlayer pattern 120, a second insulating interlayer is formed on the contact 105 and the first insulating interlayer pattern 110. In one example embodiment of the present invention, the second insulating interlayer may be formed, for example, using an oxide such as BPSG, PSG, USG, SOG, PE-TEOS, or HDP-CVD oxide. In another example embodiment of the present invention, the second insulating interlayer may be formed using a doped oxide having a dielectric constant of less than about 3.5. Examples of the doped oxide having the dielectric constant of less than about 3.5 may include such as carbon-doped oxide (SiOC), hydrogen silsesquioxane (HSQ, SiOH), or methyl silsesquioxane (MSQ, $SiOCH_3$).

For example, the second insulating interlayer may be formed by spin-coating and baking hydrogen silsesquioxane (HSQ). Then, the formation of a parasitic capacitor between the lower structures and a metal wire may be prevented or reduced.

A mask pattern (not shown) is formed on the second insulating interlayer. The second insulating interlayer exposed by the mask pattern is selectively etched to form an opening 122 exposing the contact 105. In this manner, the second insulating interlayer is patterned to form the second insulating interlayer pattern 120. Then, the mask pattern is removed from the second insulating interlayer pattern 120. When the mask pattern is a photoresist pattern, the mask pattern may be removed by a plasma ashing process and a cleaning process.

In one example embodiment of the present invention, before forming the second insulating interlayer, an etch stop layer (not shown) may be further formed on the contact 105 and the first insulating interlayer pattern 110. The etch stop layer may prevent or reduce etching damage to the contact 105, which can occur in an etching process for forming the opening 122 in the second insulating interlayer. The etch stop layer may be formed to have a thickness of about 10 Å to about 150 Å. Also, the etch stop layer may be formed using a nitride or a metal oxide having an etching selectivity relative to the second insulating interlayer. The etch stop layer on the contact 105 may be removed by a wet etching process after forming the opening 122 in the second insulating interlayer.

Figure 4:
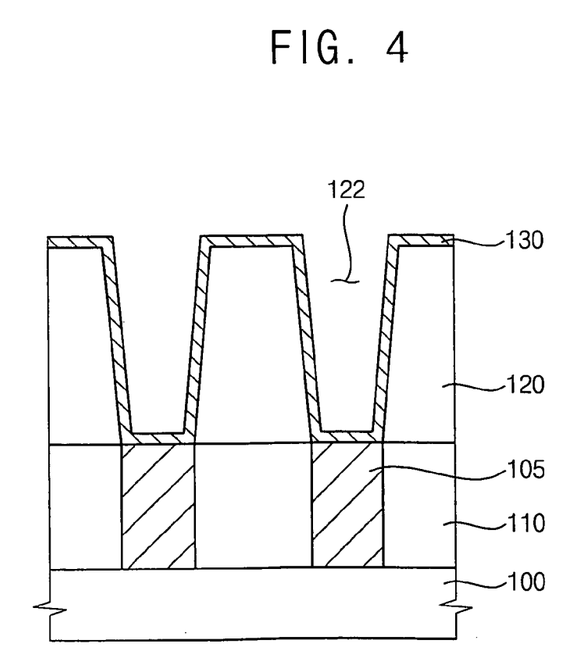

FIG. 4 is a cross-sectional view for describing a process of forming a barrier metal layer.

Referring to FIG. 4, a barrier metal layer 130 is conformably formed on a bottom and sidewalls of the opening 122, and on the second insulating interlayer pattern 120. The barrier metal layer 130, which does not fill the opening 122, may be formed to have a substantially uniform thickness.

The barrier metal layer 130 may serve to prevent or reduce aluminum in an aluminum wire formed on the barrier metal layer 130 from diffusing into the second insulating interlayer pattern 120. The barrier metal layer 130 may have a good adhesive characteristic and a low contact resistance. In addition, the barrier metal layer 130 may be highly resistant to a thermal stress and a mechanical stress. In one example embodiment of the present invention, the barrier metal layer 130 may be formed in a single-layered structure of a titanium (Ti) layer or a titanium nitride (TiN) layer. In another example embodiment of the present invention, the barrier metal layer 130 may be formed in a multi-layered structure of a titanium/titanium nitride (Ti/TiN) layer. For example, the barrier metal layer 130 is formed using titanium. When the barrier metal layer 130 is formed using titanium, the barrier metal layer 130 may effectively prevent or reduce a metal from diffusing into the second insulating interlayer pattern 120 and may have a good electrical conductivity.

In one example embodiment of the present invention, the barrier metal layer 130 may be formed using titanium to have a thickness of about 100 Å to about 500 Å. When a thickness of the barrier metal layer 130 is above about 500 Å, a contact resistance with the contact 105 may increase. When the thickness of the barrier metal layer 130 is below about 100 Å, the diffusion of a metal and the generation of particles may not be effectively prevented. Therefore, the thickness of the barrier metal layer 130 may preferably be in a range of about 100 Å to about 500 Å.

Figure 5:
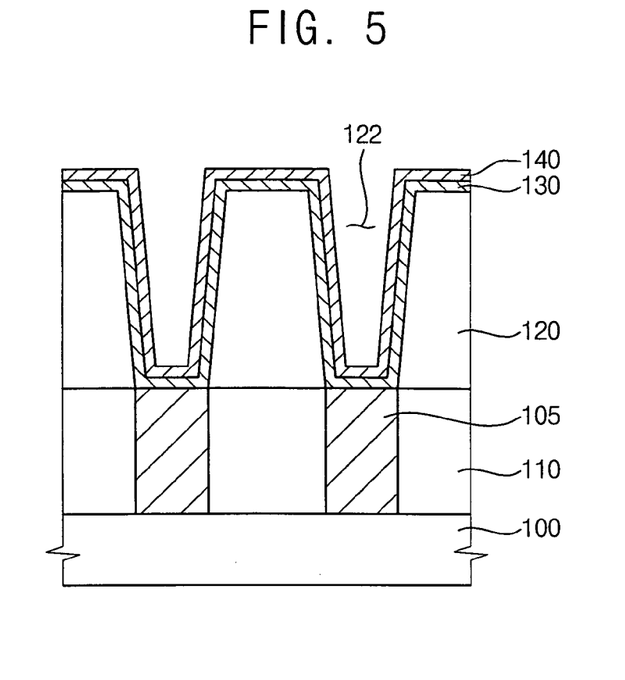

FIG. 5 is a cross-sectional view illustrating a process for forming a first aluminum layer as a seed layer.

Referring to FIG. 5, a first aluminum layer 140 is formed on the barrier metal layer 130. The first aluminum layer 140 may be formed by a CVD process using an organic aluminum precursor according to embodiments of the present invention. The first aluminum layer 140. may serve as a seed layer.

An organic aluminum precursor represented by one of the chemical formulae 1 through 4 is applied to the semiconductor substrate 100 having the barrier metal layer 130. Here, an example of the organic aluminum precursor represented by the chemical formula 1 is a dimethylamino-2-methylpropyl methyl aluminum hydride precursor. Further, an example of the organic aluminum precursor represented by the chemical formula 4 is an aluminum boro-hydride trialkylamine precursor.

Since the organic aluminum precursor exhibits a greater evaporation degree than that of the MPA precursor at substantially the same temperature, the organic aluminum precursor may exhibit greater stability than that of the MPA precursor at room temperature. Therefore, when the organic aluminum precursor is applied to the semiconductor substrate 100, the generation of aluminum particles may be suppressed.

The organic aluminum precursor applied to the semiconductor substrate is thermally decomposed to release the ligands from the aluminum of the organic aluminum precursor, thereby generating pure aluminum atoms.

Aluminum decomposed from the organic aluminum precursor is continuously chemisorbed on the barrier metal layer 130. A first aluminum layer 140 is formed on the barrier metal layer 130 by the chemisorbing aluminum.

The first aluminum layer 140 may serve as a seed layer which may improve a fluidity of a metal to be deposited in a subsequent process, and may allow the metal more easily flow into the opening 122. In addition, the first aluminum layer 140 as a seed layer may improve an adhesive characteristic of the metal.

The first aluminum layer 140 may be formed to have a substantially uniform thickness on the surface of the barrier metal layer 130. When a thickness of the first aluminum layer 140 is not uniform, the metal may not properly flow and then a void may be generated.

The first aluminum layer 140 may have a very thin thickness so as to not fill up the opening 122 having a small diameter. Thus, the first aluminum layer 140 may be formed by a process using a material favorable to step coverage. Additionally, the first aluminum layer 140 may be formed at a relatively low temperature to prevent or reduce thermal stress related damage to conductive structures located below the first aluminum layer 140.

The first aluminum layer 140 may be formed by a CVD process or a cyclic CVD process to satisfy the above properties.

Figure 6:
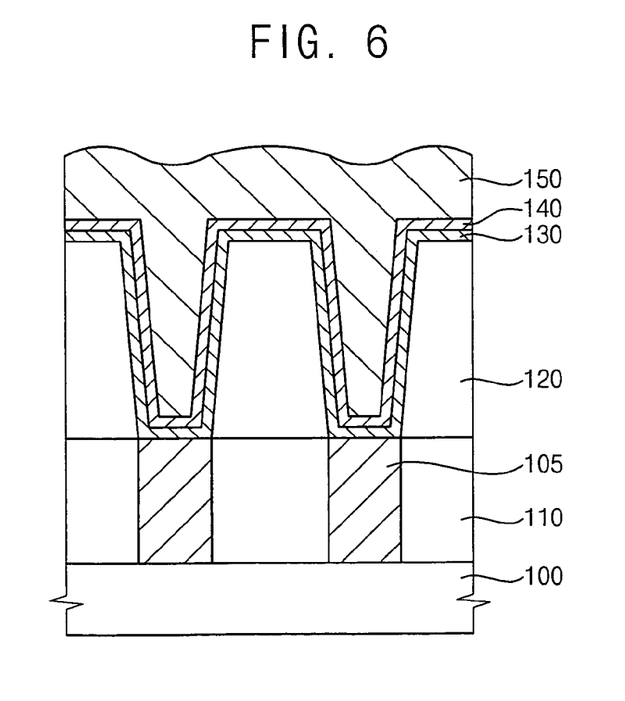

FIG. 6 is a cross-sectional view for describing a process of forming a second aluminum layer that fills the opening 122.

Referring to FIG. 6, a preliminary second aluminum layer is formed on the first aluminum layer 140 to fill the opening 122. The preliminary second aluminum layer may be formed by a physical vapor deposition (PVD) process. The PVD process may include a direct current sputtering process, an alternating current sputtering process, a direct current magnetron sputtering process, etc. For example, the preliminary second aluminum layer is formed by a direct current sputtering process.

A heat treatment is performed on the preliminary second aluminum layer at a temperature of about 350° C. to about 550° C. for a few seconds to hundreds of seconds to let the preliminary second aluminum layer reflow. A reflow process may be performed under a vacuum atmosphere to prevent an oxidation of the preliminary second aluminum layer. A second aluminum layer 150 is formed by the reflow process.

The second aluminum layer 150 may fill the opening 122 without a void and have a planarized surface. Because an oxide layer possibly disturbing a reflow of the preliminary second aluminum layer may not be formed on the first aluminum layer 140, the opening 122 may be filled up with the second aluminum layer 150 without any voids.

In one example embodiment of the present invention, an aluminum wire having favorable electrical conductivity may be formed without particles.

Synthesis for Dimethylamino-2-Methylpropyl Methyl Aluminum Hydride 12.90 g of magnesium (530 mmol), 60 g of dimethylamino-2methylpropylchloride (445 mmol) and 500 ml of diethyl ether were reacted with one another in a flask to synthesize a first Grignard reagent. 17.69 g of $AlCl_3$ (132 mmol) was added to the first Grignard reagent. The $AlCl_3$ and the first Grignard reagent were stirred for about six hours. The $AlCl_3$ and the first Grignard reagent were filtered to prepare a filtrate. The filtrate was concentrated and refined to obtain $AlL_3(L=CH_2CH(CH_3)CH_2NMe_2)$ as a second Grignard reagent.

1,000 ml of n-hexane was poured into a flask under an argon gas atmosphere. 25.44 g of $AlCl_3$ (190 mmol) and 21.72 g of $LiAlH_4$ (572 mmol) were then poured into the flask in which the n-hexane was contained. The n-hexane, the $AlCl_3$ and the $LiAlH_4$ were poured into an ice bath with diethyl ether being slowly added to synthesize an $AlH_3$ solution. 44.02 g of trimethylaluminum (610 mmol) and the $AlL_3$ $(L=CH_2CH(CH_3)CH_2NMe_2)$ were poured in-situ into the $AlH_3$ solution to form a mixed solution. The mixed solution was stirred for about three hours and heated to a room temperature of about 25° C. to remove solvents from the mixed solution. The mixed solution without the solvents was refined by distillation under reduced pressure to obtain a colorless liquid dimethylamino-2-methylpropyl methyl aluminum hydride.

Synthesis for Aluminum Boro-Hydride Trialkylamine 453.32 g of $AlCl_3$ and 180.63 g of $LiAlH_4$ were diluted with 2 L and 1.5 L of ethers, respectively. The diluted $AlCl_3$ and $LiAlH_4$ solutions were maintained at a temperature of about 30° C. The $AlCl_3$ solution was added to a flask in which the $LiAlH_4$ solution was contained. A trimethylamino ($N-Me_3$) gas was introduced into the flask through a pipe to react the trimethylamino ($N-Me_3$) gas with the $AlCl_3$ and the $LiAlH_4$ for about five hours, thereby synthesizing a $ClAlH_2NMe_3$ solution. The $ClAlH_2NMe_3$ solution was filtered to remove solvents from the $ClAlH_2NMe_3$ solution. 514.44 g of $NaBH_4$ was diluted with 2 L of ether. The $ClAlH_2NMe_3$ solution was dropped to the diluted $NaBH_4$ solution for about 30 minutes. The $ClAlH_2NMe_3$ solution and the diluted $NaBH_4$ solution were reacted with each other for about 20 hours to form a chemical compound solution. The chemical compound solution was filtered to remove solvents in the chemical compound solution, thereby obtaining a chemical compound. The chemical compound was refined by distillation under reduced pressure to obtain a colorless liquid aluminum boro-hydride trialkylamine.

Evaluating Vapor Pressures in Accordance with Temperature Changes

Figure 7:
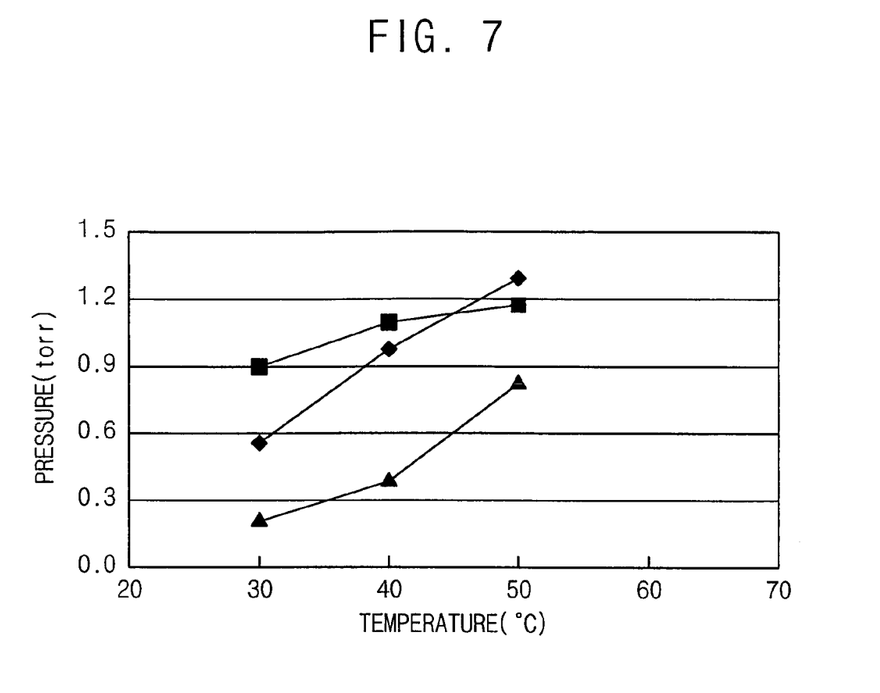
FIG. 7 is a graph illustrating vapor pressures relative to temperature of an MPA precursor and organic aluminum precursors in accordance with example embodiments of the present invention.

FIG. 7 is a graph illustrating vapor pressures relative to temperature of an MPA precursor and two organic aluminum precursors in accordance with the example embodiments of chemical formulae 1 and 4 of the present invention.

The organic aluminum precursors of the example embodiments and an MPA precursor were introduced into canisters, respectively. Vapor pressures in the canisters were measured with internal temperatures of the canisters being increased by 5° C. per minute.

In FIG. 7, a curved line —■— indicates vapor pressures of the organic aluminum precursor represented by the chemical formula 1, in particular, dimethylamino-2-methylpropyl methyl aluminum hydride, a curved line —◆— represents vapor pressures of the organic aluminum precursor represented by the chemical formula 4, in particular, aluminum boro-hydride trialkylamine, and a curved line —▲— represents vapor pressures of the MPA precursor.

As shown in FIG. 7, when the organic aluminum precursor represented by the chemical formula 1 is heated to a temperature of 50° C. by 5° C. per minute, the organic aluminum precursor exhibits vapor pressures of about 0.9 torr at a temperature of about 30° C., about 1.1 torr at a temperature of about 40° C., and about 1.2 torr at a temperature of about 50° C. Further, the organic aluminum precursor represented by the chemical formula 4 exhibits vapor pressures of about 0.55 torr at a temperature of about 30° C., about 0.97 torr at a temperature of about 40° C., and about 1.3 torr at a temperature of about 50° C. In contrast, the MPA precursor exhibits vapor pressures of about 0.2 torr at a temperature of about 30° C., about 0.42 torr at a temperature of about 40° C., and about 0.8 torr at a temperature of about 50° C.

As shown in the results above, it can be noted that the organic aluminum precursors of the present invention may exhibit vapor pressures of no less than about two times that of the MPA precursor at substantially the same temperature. That is, the organic aluminum precursors of the present invention may be advantageously evaporated at a temperature which is lower than that of the MPA precursor.

Evaluating Resistances in Accordance with Temperature Variations

Figure 8:
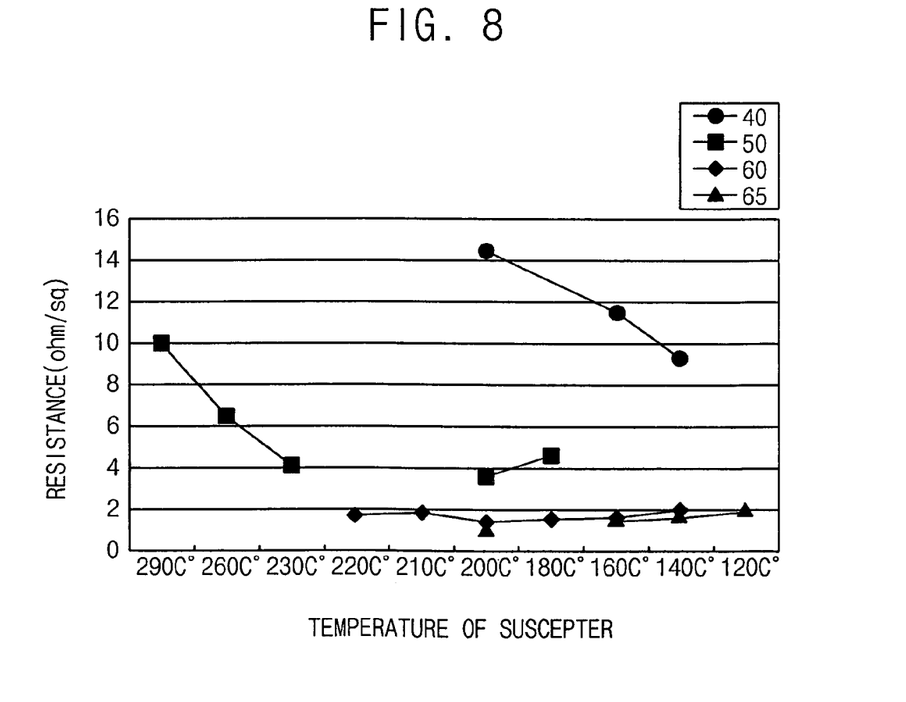
FIG. 8 is a graph illustrating resistances relative to suscepter temperature at different canister temperatures of an aluminum layer in accordance with an example embodiment of the present invention.

FIG. 8 is a graph illustrating resistances relative to suscepter temperature at different canister temperatures of an aluminum layer formed in accordance with an example embodiment of the present invention.

Aluminum layers were formed on semiconductor substrates while changing the temperature of a suscepter to heat the semiconductor substrates and a temperature of canister in which the organic aluminum precursor, i.e., dimethylamino-2-methylpropyl methyl aluminum hydride, is contained. Resistances of the aluminum layers were then measured.

In FIG. 8, a curved line —●— represents resistances when the canister had a temperature of about 40° C., a curved line —■— indicates resistances when the canister had a temperature of about 50° C., a curved line —□— represents resistances when the canister had a temperature of about 60° C., and a curved line —▲— represents resistances when the canister had a temperature of about 65° C.

As shown in FIG. 8, the aluminum layer may be optimally formed when the suscepter has a temperature of about 140° C. and the canister has a temperature of about 60° C. to about 65° C.

According to the present invention, when the CVD process is performed using the organic aluminum precursor, the organic aluminum precursor may not be decomposed, because the organic aluminum precursor may exhibit thermal and chemical stability. Thus, the aluminum wiring formed using the organic aluminum precursor may exhibit good electrical conductivity without particles such as carbon, aluminum, etc. Further, the aluminum wiring may have a flat upper face and provide good step coverage.

Having described the preferred embodiments of the present invention, it is noted that modifications and variations can be made by persons skilled in the art in light of the above teachings. It is therefore to be understood that changes may be made in the particular embodiment of the present invention disclosed which is within the scope and the spirit of the invention outlined by the appended claims.

What is claimed is:

1. A method of manufacturing a metal wiring, comprising:
    applying an organic aluminum precursor to a substrate, the organic aluminum precursor having aluminum as a central metal;
    thermally decomposing the organic aluminum precursor over the substrate; and
    depositing the thermally decomposed organic aluminum precursor on the substrate to form an aluminum layer on the substrate,
    wherein the organic aluminum precursor includes dimethylamino-2-methylpropyl methyl aluminum hydride,
    wherein the organic aluminum precursor is contained in a canister at a temperature of about 60° C. to about 65° C. prior to application of the organic aluminum precursor to the substrate,
    wherein the organic aluminum precursor is decomposed on the substrate supported by a suscepter having a temperature of about 120° C. to 220° C., and
    wherein the aluminum layer has a resistance of less than about 2 ohm/sq, and
    wherein the organic aluminum precursor has a vapor pressure of about 1.1 torr to about 1.3 torr in the canister at a temperature of about 60° C.

2. The method of claim 1, wherein the organic aluminum precursor is applied to the substrate with a carrier gas.

3. The method of claim 1, wherein depositing the thermally decomposed organic aluminum precursor on the substrate is carried out by a chemical vapor deposition (CVD) process or a cyclic CVD process.

4. The method of claim 1, wherein the vapor pressure of the organic aluminum precursor is measured while an internal temperature of the canister being increased by 5° C. per minute.

5. A method of manufacturing a metal wiring, comprising:
    applying an organic aluminum precursor to a substrate, the organic aluminum precursor having aluminum as a central metal;
    thermally decomposing the organic aluminum precursor over the substrate; and
    depositing the thermally decomposed organic aluminum precursor on the substrate to form an aluminum layer on the substrate,
    wherein the organic aluminum precursor includes dimethylamino-2-methylpropyl methyl aluminum hydride,
    wherein the organic aluminum precursor is contained in a canister at a temperature of about 60° C. to about 65° C. to application of the organic aluminum precursor to the substrate,
    wherein the organic aluminum precursor is decomposed on the substrate supported by a suscepter having a temperature of about 120° C. to about 220° C., and
    wherein the organic aluminum precursor has a vapor pressure about 1.1 torr to about 1.3 torr in the canister at a temperature of about 60° C.

6. The method of claim 5, wherein the vapor pressure of the organic aluminum precursor is measured while an internal temperature of the canister being increased by 5° C. per minute.

7. The method of claim 5, wherein the aluminum layer has a resistance of less than about 2 ohm/sq.

* * * * *